US012397293B2

(12) United States Patent
Govyadinov et al.

(10) Patent No.: US 12,397,293 B2
(45) Date of Patent: Aug. 26, 2025

(54) SORTING A DROPLET INCLUDING A BIOLOGIC SAMPLE

(71) Applicant: HEWLETT-PACKARD DEVELOPMENT COMPANY, L.P., Spring, TX (US)

(72) Inventors: Alexander Govyadinov, Corvallis, OR (US); Viktor Shkolnikov, Palo Alto, CA (US)

(73) Assignee: HEWLETT-PACKARD DEVELOPMENT COMPANY, L.P., Spring, TX (US)

( * ) Notice: Subject to any disclaimer, the term of this patent is extended or adjusted under 35 U.S.C. 154(b) by 869 days.

(21) Appl. No.: 17/634,787

(22) PCT Filed: Dec. 4, 2019

(86) PCT No.: PCT/US2019/064505
§ 371 (c)(1),
(2) Date: Feb. 11, 2022

(87) PCT Pub. No.: WO2021/112841
PCT Pub. Date: Jun. 10, 2021

(65) Prior Publication Data
US 2022/0323958 A1 Oct. 13, 2022

(51) Int. Cl.
*B01L 3/00* (2006.01)
*B01L 7/00* (2006.01)
*C12Q 1/6844* (2018.01)

(52) U.S. Cl.
CPC ......... *B01L 3/502753* (2013.01); *B01L 7/525* (2013.01); *C12Q 1/6844* (2013.01); *B01L 2200/0652* (2013.01); *B01L 2200/10* (2013.01); *B01L 2200/16* (2013.01); *B01L 2300/0663* (2013.01); *B01L 2400/086* (2013.01)

(58) Field of Classification Search
CPC ............... B01L 3/502753; B01L 7/525; B01L 2200/0652; B01L 2200/10; B01L 2200/16; B01L 2300/0663; B01L 2400/086; B01L 2300/161; B01L 2200/0673; B01L 2300/0864; B01L 2400/0406; B01L 2400/0457; B01L 3/502761; B01L 3/502784; C12Q 1/6844
See application file for complete search history.

(56) References Cited

U.S. PATENT DOCUMENTS

| | | | |
|---|---|---|---|
| 9,030,215 B2 | 5/2015 | Lee et al. | |
| 9,534,216 B2 | 1/2017 | Link | |
| 9,752,141 B2 * | 9/2017 | Link | C12Q 1/686 |
| 10,221,437 B2 | 3/2019 | Weitz et al. | |
| 2018/0327813 A1 | 11/2018 | Chen et al. | |

FOREIGN PATENT DOCUMENTS

| | | |
|---|---|---|
| WO | WO-2014028378 | 2/2014 |
| WO | WO-2016040476 | 3/2016 |
| WO | WO-2018213643 | 11/2018 |

OTHER PUBLICATIONS

Horvath et al: "Sorting by interfacial tension (SIFT): Label-free enzyme sorting using droplet microfluidics", Analytica Chimica Acta, Elsevier, Amsterdam, NL, vol. 1089, Aug. 17, 2019.

Pan et al.; "Sorting by interfacial tension (SIFT): label-free selection of live cells based on single-cell metabolism"; Lab Chip; 19, 1344-1351; 2019.

Afrasiabi et al.; "Integration of a Droplet-Based Microfluidic System and Silicon Nanoribbon FET Sensor"; Micromachines; 7, 134; 2016.

Wang et al.; "Real-time DNA Amplification and Detection System Based on a CMOS Image Sensor"; Analytical Sciences; 32, 653-658; 2016.

* cited by examiner

*Primary Examiner* — Narayan K Bhat
(74) *Attorney, Agent, or Firm* — Foley & Lardner LLP

(57) ABSTRACT

Examples herein involve sorting a droplet including a biologic sample. In a particular example, sorting a droplet including a biologic sample includes generating a droplet including a biologic sample and a pH sensitive surfactant, and heating a nucleic acid molecule in the biologic sample. The pH sensitive surfactant may change the surface tension of the droplet responsive to amplification of the nucleic acid molecule. The droplet may be sorted into one of a plurality of sorting lanes based on the surface tension of the droplet, where a sorting lane among the plurality of sorting lanes is associated with droplets including the amplified nucleic acid molecule. A determination of whether the droplet includes the amplified nucleic acid molecule may be performed by detecting passage of the droplet in one of the plurality of sorting lanes.

10 Claims, 12 Drawing Sheets

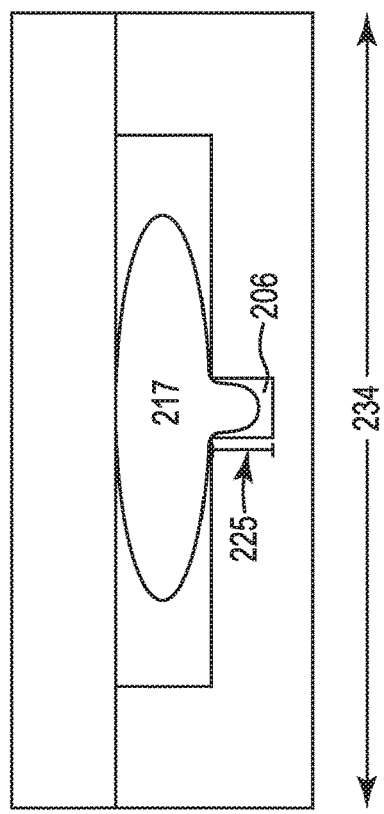
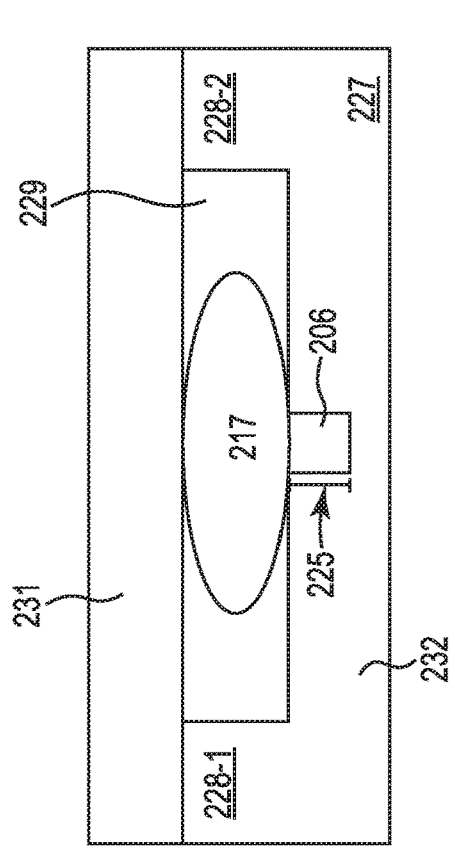

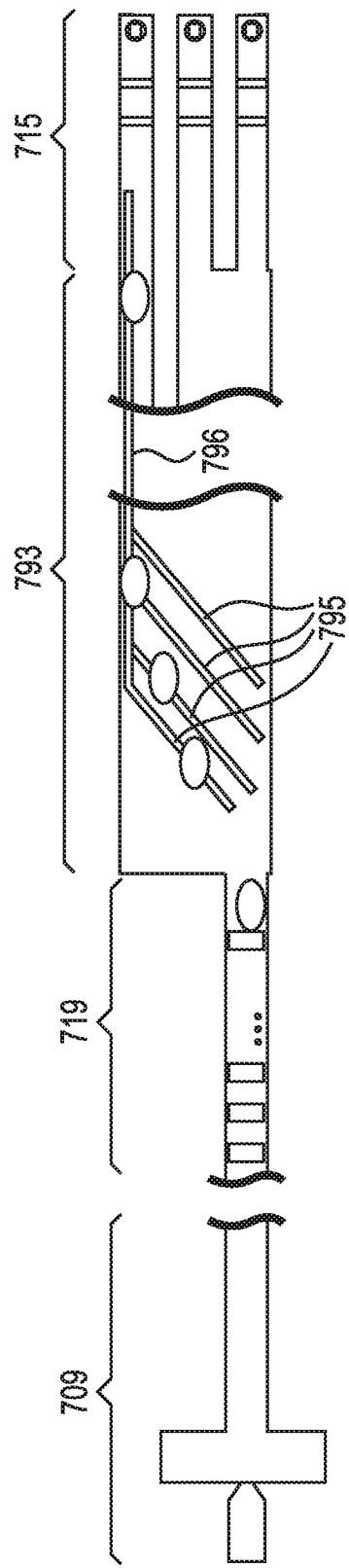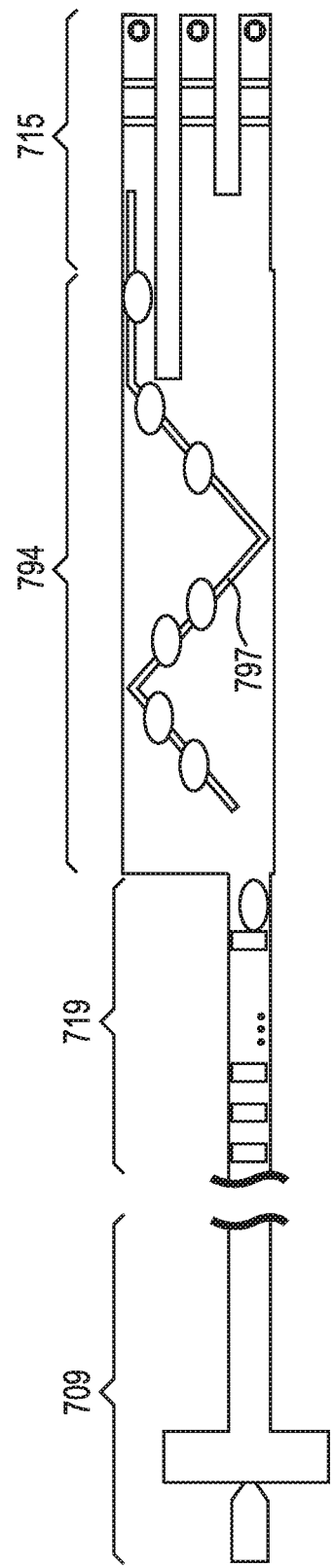

SORTING A DROPLET INCLUDING A BIOLOGIC SAMPLE

CROSS-REFERENCE TO RELATED APPLICATIONS

This Utility Patent Application is a U.S. National Stage filing under 35 U.S.C. § 371 of PCT/US2019/064505, filed Dec. 4, 2019, incorporated by reference herein.

BACKGROUND

Microfluidics has wide ranging application to numerous disciplines such as engineering, chemistry, biochemistry, biotechnology, and so on. Microfluidics can involve the manipulation and control of small volumes of fluid within various systems and devices such as inkjet printheads, lab-on-chip devices, and other types of microfluidic chip devices.

BRIEF DESCRIPTION OF THE DRAWINGS

FIGS. 2B, 2C, 2D, 2E, and 2F illustrate example cross-sections of a surface tension sorter, consistent with the present disclosure.

FIGS. 7A, 7B, and 7C illustrate example apparatuses for sorting a droplet including a biologic sample, consistent with the present disclosure.

DETAILED DESCRIPTION

Figure 1:
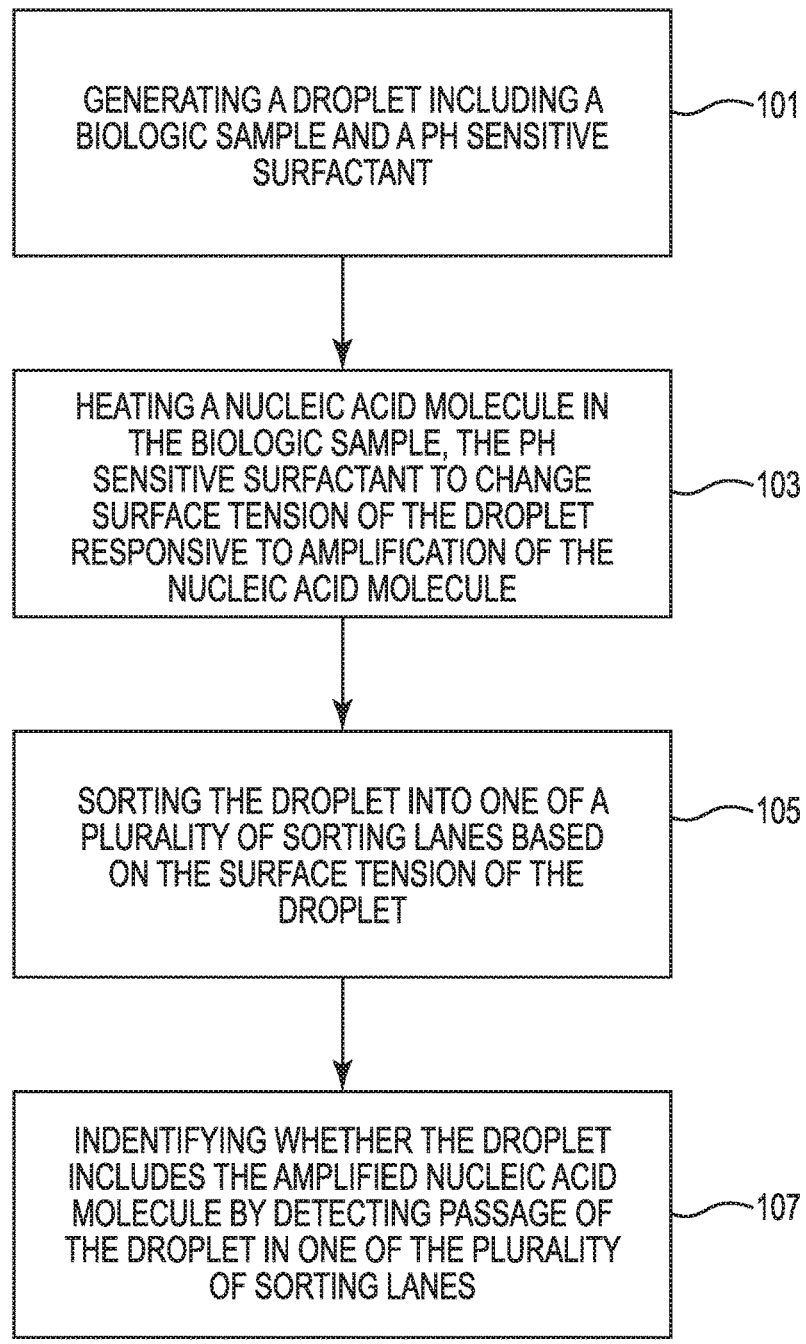
FIG. 1 illustrates an example method for sorting a droplet including a biologic sample, consistent with the present disclosure.

In the following detailed description, reference is made to the accompanying drawings which form a part hereof, and in which is shown by way of illustration specific examples in which the disclosure may be practiced. It is to be understood that other examples may be utilized, and structural or logical changes may be made without departing from the scope of the present disclosure. The following detailed description, therefore, is not to be taken in a limiting sense, and the scope of the present disclosure is defined by the appended claims. It is to be understood that features of the various examples described herein may be combined, in part or whole, with each other, unless specifically noted otherwise.

Polymerase chain reaction (PCR) is a method used in molecular biology to make many copies of a nucleic acid segment. Using PCR, a single copy (or more) of a nucleic acid sequence is exponentially amplified to generate thousands to millions or more copies of that particular nucleic acid segment. Digital polymerase chain reaction (digital PCR, DigitalPCR, dPCR, or dePCR) refers to or includes PCR methods that can be used to directly quantify and clonally amplify nucleic acids strands including DNA, cDNA or RNA. Similarly, Droplet Digital PCR (ddPCR) is a method for performing digital PCR that is based on water-oil emulsion droplet technology. A sample is fractionated into a plurality of droplets, such as 20,000 droplets, and PCR amplification of the template molecules occurs in each individual droplet.

The difference between dPCR (including ddPCR) and PCR lies in the method of measuring nucleic acid amounts. PCR is based on the theory that amplification of nucleic acid strands is exponential. Therefore, nucleic acids may be quantified by comparing the number of amplification cycles and amount of PCR end-product to those of a reference sample. However, the actual amount of nucleic acid amplified may not directly correlate with the number of amplification cycles, and therefore such measurements may be inaccurate. For instance, initial amplification cycles may not be exponential, PCR amplification may plateau after an uncertain number of cycles, and low initial concentrations of target nucleic acid molecules may not amplify to detectable levels. In contrast, dPCR involves partitioning the initial solution into tens of thousands of nano-liter sized droplets, where a separate PCR reaction takes place in each droplet. After multiple PCR amplification cycles, the samples are checked for fluorescence with a binary readout of "0" or "1". However, dPCR uses expensive optical devices for readout of reaction results, in addition to the device for nucleic acid amplification, which in turn results in high instrument cost and high assay cost.

In accordance with examples of the present disclosure, nucleic acid amplification may be performed and detected without the use of separate optical detection devices, and within a single apparatus. The detection of amplified nucleic acids may be transduced via a pH change in a droplet within the apparatus, and transduced mechanically via droplet location. The droplet location may then be determined by impedance based or capacitive based sensing. Performing the amplification and detection of nucleic acids on a single apparatus may reduce the overall instrument cost and therefore the assay cost of nucleic acid amplification.

Turning now to the figures, FIG. 1 illustrates an example method for sorting a droplet including a biologic sample, consistent with the present disclosure. The present disclosure relates to a method, comprising: generating a droplet including a biologic sample and a pH sensitive surfactant; heating a nucleic acid molecule in the biologic sample, the pH sensitive surfactant to change surface tension of the droplet responsive to amplification of the nucleic acid molecule; sorting the droplet into one of a plurality of sorting lanes based on the surface tension of the droplet, wherein a sorting lane among the plurality of sorting lanes is associated with droplets including the amplified nucleic acid molecule; and identifying whether the droplet includes the amplified nucleic acid molecule by detecting passage of the droplet in one of the plurality of sorting lanes.

As illustrated in FIG. 1, the method includes generating a droplet including a biologic sample and a pH sensitive surfactant at 101. In some examples, the method includes generating a droplet including a biologic sample and a pH sensitive surfactant includes separating the biologic sample into a plurality of droplets, each droplet of the plurality of droplets including reagents for thermal amplification and the pH sensitive surfactant. A biologic sample may be fractionated into a plurality of droplets, such as 20,000 droplets, each including a portion of the original biologic sample. Several different methods may be used to partition the biologic sample and generate a droplet or a plurality of droplets. Non-limiting example methods for generating a droplet include using microwell plates, capillaries, oil emulsion, and arrays of miniaturized chambers with nucleic acid binding surfaces.

Each droplet generated may include a plurality of components to facilitate nucleic acid amplification. Once the sample is partitioned into the plurality of droplets, PCR may be performed on each of the plurality of droplets. PCR is a temperature-mediated process involving cycling a reaction volume, or mixture, between set temperatures. Accordingly, the biologic sample (sometimes referred to as a reaction volume or mixture) which is partitioned into a plurality of droplets contains one or more nucleic acid(s) sequences to be amplified, which is termed the "template" strand. By partitioning the biologic sample into a plurality of droplets, each droplet may include at most one copy of the nucleic acid sequence to be amplified, or one template strand. Similarly, each droplet may include a reagent or a plurality of reagents for amplification of the nucleic acid, as well as a pH sensitive surfactant.

Several reagents may be used in PCR and may be included in the plurality of droplets. Examples of such reagents include an enzyme that polymerizes new nucleic acid strands (referred to as polymerase), two or more nucleic acid primers specific for targeting the sequence to be amplified, a mixture of deoxyribonucleotide triphosphates (dNTPs), and a buffer solution. Examples of the polymerase enzyme include, but are not limited to, DNA polymerase such as Taq DNA polymerase, and reverse transcriptase. Examples of the buffer solution include components such as bivalent cations, including magnesium (Mg) or manganese (Mn) ions and monovalent cations, such as potassium (K) ions, among others. Additional reagents and/or components which may be included in each droplet include reporter molecules such as fluorophores or molecules that generate an electrochemical signal. Together, these components may be referred to as "master mix" and form the environment conducive to nucleic acid amplification.

At 103 the method includes heating a nucleic acid molecule in the biologic sample, such that the pH sensitive surfactant may change surface tension of the droplet responsive to amplification of the nucleic acid molecule. PCR is a temperature-mediated process involving cycling a reaction volume, or mixture, between set temperatures. The reaction volume/mixture contains one or more nucleic acid(s) sequences to be amplified, which is termed the "template" strand. In the reaction volume, the template strand may be in a double-strand form with its complementary strand. If the template and complimentary strands are present as a double-strand nucleic acid molecule, such as a deoxyribonucleic acid (DNA) double helix, this double-strand molecule is denatured in a first step of PCR. In such a process, the double-strand nucleic acid molecule is split into two single nucleic acid strands. In this first step of PCR, the two strands of a double-stranded molecule are physically separated at a high temperature in a process called denaturation or melting. Denaturation occurs at a temperature, which is termed the denaturing temperature. The reaction volume/mixture further contains at least two primers. "Primers" refer to or include short single-strand nucleic acid segments, which are also known as oligonucleotides, with sequences that are either partially or entirely complementary to the template (target) nucleic acid sequence. One of the primers is termed a forward primer while the other is termed a reverse primer.

In the second step of PCR, the temperature of the volume/mixture is lowered, and the primers "anneal" (hybridize, or bind), to their complementary sequences on the target nucleic acid sequence. The two, now double-stranded, nucleic acid strands then become templates for an enzymatic reaction using a polymerase to replicate/synthesize/assemble a new nucleic acid strand from free nucleotides that are also found in the reaction volume/mixture. The forward primer hybridizes to a sequence in the sense strand while the reverse primer hybridizes to a sequence in the antisense strand. The hybridization of the primers with the complementary sequences of the sense or antisense strand is termed annealing. This second step takes place at a temperature termed the annealing temperature. The droplet formed at 101, includes the volume/mixture including a nucleic acid, for nucleic acid amplification.

The reaction volume/mixture may further contain a polymerase enzyme. In a third step, the polymerase synthesizes a copy of the complement starting from the forward primer and synthesizes a copy of the sense strand starting from the 5' end of the reverse primer. Throughout the synthesis, the copy of the antisense strand also hybridizes with the sense strand and the copy of the sense strand hybridizes with the antisense strand. This third step is termed elongation and is carried out at a temperature called the elongation temperature. After the elongation step, the first, second, and third steps are repeated until the extent of amplification is achieved, wherein multiple copies of the sense and antisense strands are made. As PCR progresses, the nucleic acid generated is itself used as a template for replication, setting in motion a chain reaction in which the original nucleic acid template is exponentially amplified. During nucleic acid amplification, the pH of the reaction volume may change proportional to the amount of amplified target molecules.

The pH sensitive surfactant may change surface tension of the droplet responsive to amplification of the nucleic acid molecule. The pH is a measure of the hydrogen ion concentration of a solution (in this instance, the droplet). Solutions with a high concentration of hydrogen ions have a low pH (acidic) and solutions with a low concentration of hydrogen ions have a high pH (alkaline). When a polymerase enzyme incorporates a dNTP into a nucleic acid strand, the released by-products include a hydrogen ion. Accordingly, the amount of nucleic acid amplification may result in a significant change in the droplet from an initial alkaline (high) pH to a final acidic (low) pH.

In various examples, the pH sensitive surfactant includes compounds with an ionizable group such as a carboxylic acid and/or an amine group. Examples of such surfactant include compounds with 2-pyrrolidone headgroups, such as N,N'-dialkyl-N,N'-di(ethyl-2-pyrrolidone)ethylenediamine (Di-CnP, where n=6, 8 10, 12). Another example pH sensitive surfactant is N-dodecyl-1,3-diaminopropane (C12NCnN, illustrated below), which includes a single hydrophobic carbon chain, coupled to a diamine hydrophilic function.

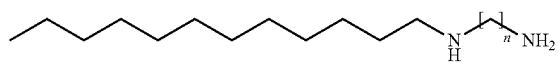

Such pH sensitive surfactants demonstrate significant changes in viscosity, solubility, and stability with a change in pH. For instance, C12NC3N evolves from spherical micelles at a pH of 1.98 to rod-like micelles at a pH of 8.00 into wormlike micelles at a pH of 9.01, to perforated vesicles at a pH of 9.97.

If the nucleic acid amplification is successful, such that the target nucleic acid is present, then the pH in the droplet will change. Amplification reactions may be performed under low buffering conditions, where a change in pH can be detected and quantitatively measured using the ion sensitive field effect transistor (ISFET) sensors, temperature sensors, signal processing and control circuitry. A correlation between a normalized change in pH and a total amount of accumulated nucleic acid may help identify the number of copies of a nucleic acid molecule in a sample. Therefore, the pH of the sample can be correlated with a number of copies of the nucleic acid molecule.

In various examples, the surface tension and/or the pH of each droplet may be measured. The surface tension of each droplet may be measured using a tensiometer. As used herein, a tensiometer refers to or includes an instrument used to measure the surface tension of liquids. Surface tension refers to or includes the contractive quality of the surface of a liquid that allows it to resist external force. A variety of tensiometers may be used. Non-limiting examples include, a goniometer, a Du Noüy Ring Tensiometer, Wilhelmy Plate Tensiometer, and a bubble pressure tensiometer. The pH of each droplet may be measured using a pH electrode and/or a pH strip. An example pH electrode includes a glass electrode. A glass electrode refers to or includes a type of ion-selective electrode made of a doped glass membrane that is sensitive to a specific ion. A pH strip refers to or includes a halochromic chemical compound which allows the pH of droplets to be determined visually.

At 105, the method includes sorting the droplet into one of a plurality of sorting lanes based on the surface tension of the droplet, where a sorting lane among the plurality of sorting lanes is associated with droplets including the amplified nucleic acid molecule. As discussed herein, sorting the droplet into one of a plurality of sorting lanes may be performed based on the surface tension of the droplet.

In various examples, a sorting lane among the plurality of sorting lanes may be associated with droplets including the amplified nucleic acid molecule. In such examples, the method includes sorting each respective droplet among the plurality of droplets into a sorting lane of the plurality of sorting lanes. Sorting each respective droplet among the plurality of droplets into a sorting lane of the plurality of sorting lanes includes sorting each respective droplet into a respective sorting lane based on pH of the respective droplet. Surface tension is impacted by pH changes. For instance, droplets with a higher pH have a higher surface tension, and droplets with a lower pH have a lower surface tension. Accordingly, a trench disposed along a length of the apparatus may separate droplets based on surface tension, and therefore by pH. As a non-limiting illustration, droplets at a pH of 7.48 have a lower surface tension, whereas droplets at a pH of 7.01 have a higher surface tension. The change in pH, and therefore change in surface tension, allows droplets with a particular surface tension to be sorted.

At 107, the method includes identifying whether the droplet includes the amplified nucleic acid molecule by detecting passage of the droplet in one of the plurality of sorting lanes. The droplet location can be determined by impedance based or capacitive based label free sensing, rather than using fluorescent or absorptive optical detection. By detecting passage of each respective droplet using an impedance sensor or capacitive based label free sensing circuitry, quantification of nucleic acid amplification may be detected. As amplification, sorting, and detection is performed on a single apparatus, the overall instrument cost and therefore the assay cost for nucleic acid amplification and detection of the same may be reduced. Additionally, sorting of droplets as described herein, may measure pH change in a droplet continuously via a change in the trench profile. This in turn enables droplet-based qualitative polymerase chain reaction (qPCR). As such, the method may include quantifying amplification of the nucleic acid molecule, by detecting passage of each respective droplet among the plurality of droplets using an impedance sensor or capacitive based label free sensing circuitry.

Figure 2A:
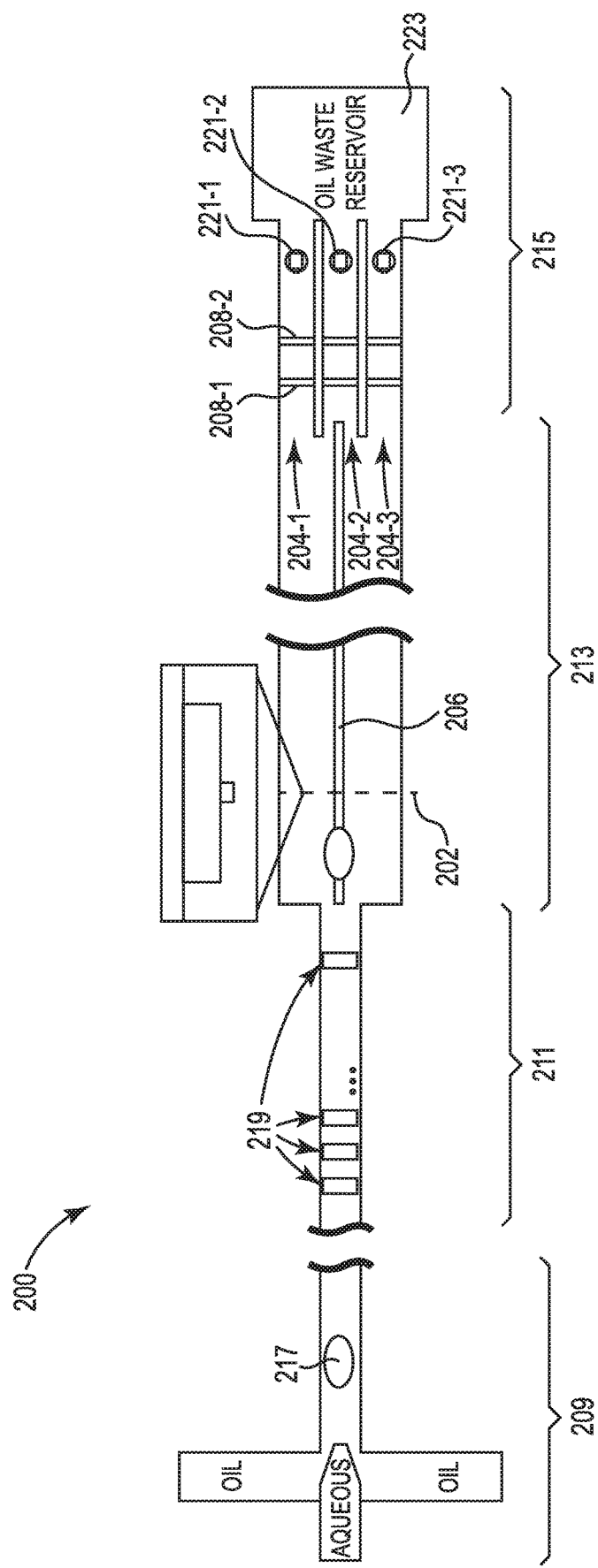
FIG. 2A illustrates an example apparatus for sorting a droplet including a biologic sample, consistent with the present disclosure.

FIG. 2A illustrates an example apparatus 200 for sorting a droplet including a biologic sample, consistent with the present disclosure. The present disclosure relates to an apparatus including a droplet generator to generate a droplet including a biologic sample and a pH sensitive surfactant; a reaction zone including a heating array for thermal amplification of a nucleic acid molecule in the biologic sample, the pH sensitive surfactant to change surface tension of the droplet responsive to amplification of the nucleic acid molecule; a surface tension-based sorter to sort the droplet into one of a plurality of sorting lanes based on the surface tension of the droplet, wherein a sorting lane among the plurality of sorting lanes is associated with droplets including the amplified nucleic acid molecule; and a droplet counter including circuitry to identify whether the droplet includes the amplified nucleic acid molecule by detecting passage of the droplet in one of the plurality of sorting lanes.

Additionally, the present disclosure relates to an apparatus with a droplet generator to generate a droplet including a biologic sample and a pH sensitive surfactant; a reaction zone including a heating array for thermal amplification of a nucleic acid molecule in the biologic sample, the pH sensitive surfactant to change surface tension of the droplet responsive to amplification of the nucleic acid molecule; a surface tension-based sorter to sort the droplet into one of a plurality of sorting lanes based on the surface tension of the droplet; and a droplet counter including circuitry to detect passage of the droplet in one of the plurality of sorting lanes and count a number of droplets in each of the plurality of sorting lanes.

The apparatus 200 is a single device for amplification of nucleic acids, and detection of the amplified nucleic acids by mechanical and electrical means rather than optical means. Equipment utilization for PCR and detection of amplified nucleic acids may be reduced by combining amplification, sorting, and detection components in a single apparatus.

As illustrated in FIG. 2A, the apparatus 200 may include a droplet generator 209 to generate a droplet 217 including a biologic sample and a pH sensitive surfactant. The droplet generator 209 may form aqueous based droplets that are suspended in oil, as may be implemented in ddPCR. Although not illustrated in FIG. 2A, the oil may be provided by a reservoir external to the apparatus 200.

As described herein, the droplet 217 may include a biologic sample including a nucleic acid, a reagent for amplification of the nucleic acid, as well as a pH sensitive surfactant. Several components and reagents may be used in PCR. Among these components are, a biologic sample that contains the target sequence(s) to be amplified, an enzyme that polymerizes new nucleic acid strands, two (or more) nucleic acid primers specific for targeting sequence, mixture of deoxyribonucleotide triphosphates (dNTPs), and a buffer solution providing a suitable chemical environment for amplification and optimum activity and stability of the polymerase. Examples of the polymerase enzyme include, but are not limited to, DNA polymerase such as Taq DNA polymerase, and reverse transcriptase. Examples of the buffer solution include components such as bivalent cations, including magnesium (Mg) or manganese (Mn) ions and monovalent cations, such as potassium (K) ions, among others. Further, PCR may include reporter molecules such as fluorophores or molecules that generate an electrochemical signal. Together, these components may be referred to as "master mix" and form the environment conducive to nucleic acid amplification.

Additionally, the apparatus 200 includes a reaction zone 211 including a heating array 219 for thermal amplification of a nucleic acid molecule in the biologic sample, where the pH sensitive surfactant may change the surface tension of the droplet responsive to amplification of the nucleic acid molecule. The heating array 219 may include a plurality of electronic heaters, spaced and/or otherwise arranged within apparatus 200 to heat the droplet 217 in a time-based sequence according to a nucleic acid amplification protocol. In various examples, the reaction zone 211 may include an external heater as opposed to embedded electronic heaters.

As described herein, the pH sensitive surfactant in the droplet 217 may cause a change in surface tension of the droplet 217 responsive to amplification of the nucleic acid molecule. In various examples, a surface tension-based sorter 213 may be arranged to sort the droplet 217 into one of a plurality of sorting lanes (204-1, 204-2, and 204-3, hereinafter referred to as sorting lanes 204) based on the surface tension of the droplet, where a sorting lane among the plurality of sorting lanes is associated with droplets including the amplified nucleic acid molecule. For instance, a particular sorting lane 204-2 among the plurality of sorting lanes 204 may be associated with droplets including the amplified nucleic acid molecule. Moreover, the particular sorting lane 204-2 may include a trench 206 which assists in the sorting of droplets. A depressed cross-section of the trench 206 permits droplets with a surface tension at or above the threshold surface tension to travel past the trench 206, and to travel a length of the apparatus to the droplet counter 215.

In various examples, the surface tension-based sorter includes a trench extending from the reaction zone 211 to the droplet counter 215. In such examples, the surface tension-based sorter includes a trench extending from the reaction zone to the droplet counter, the trench including a depressed cross-section in which droplets with a surface tension below a threshold surface tension migrate partly into the depressed cross-section. The trench 206 may extend to a particular sorting lane 204-2 among the plurality of sorting lanes 204. The particular sorting lane 204-2 may be assigned to droplets including the amplified nucleic acid molecule, and the remainder of the sorting lanes among the plurality of sorting lanes (204-1 and 204-3) may be assigned to droplets that do not include the amplified nucleic acid molecule. For instance, the trench 206 may allow droplets with a surface tension below a threshold level to be sorted into sorting lane 204-2, whereas droplets with a surface tension at or above the threshold level to be sorted into sorting lanes 204-1 or 204-3.

The droplet counter 215, in various examples, may include circuitry to identify whether the droplet includes the amplified nucleic acid molecule by detecting passage of the droplet in one of the plurality of sorting lanes. The droplet counter may therefore include circuitry to detect passage of the droplet in one of the plurality of sorting lanes and count a number of droplets in each of the plurality of sorting lanes.

The droplet counter 215 may include counting electrodes 208-1 and 208-2 (collectively referred to herein as electrodes 208). The counting electrodes 208 detect a change of impedance upon passage of a droplet in a respective sorting lane 204. Although electrode 208-1 and electrode 208-2 are illustrated as a single electrode extending a width of the apparatus 200, each of electrode 208-1 and electrode 208-2 may include separate and discrete electrodes in each of the plurality of sorting lanes 204, such that passage of a droplet in each respective sorting lane may be distinguished from passage of the droplet in a different respective sorting lane.

As illustrated in FIG. 2A, the apparatus 200 may include additional components, such as droplet ejectors 221-1, 221-2, 221-3, collectively referred to as droplet ejectors 221. Each droplet ejector includes a piezoelectric element, a thermal resistor, or other device to eject the droplets (e.g., the aqueous droplets) from the apparatus 200. Similarly, the apparatus 200 may include an oil waste reservoir 223. For instance, the droplets may be aqueous based droplets floating in oil, as may be implemented in various dPCR techniques. The oil waste reservoir 223 may capture the droplets which have transposed across the droplet counter 215 as well as the oil within which the droplets are suspended.

Further, FIGS. 2B, 2C, 2D, 2E, and 2F illustrate example cross-sections of a surface tension sorter, consistent with the present disclosure. Particularly, FIGS. 2B and 2C further illustrate example cross-sections of surface tension-based sorter 213, along plane 202, consistent with the present disclosure. Each of FIGS. 2B and 2C illustrate an example manner in which droplets may be sorted by the surface tension-based sorter 213.

The surface tension-based sorter 213 may include a trench 206 extending from the reaction zone 211 to the droplet counter 215 that allows the droplets to be sorted based on surface tension as well as by the pH of the droplet. For instance, the trench 206 may include a depressed cross-section 225 in which droplets with a surface tension below a threshold surface tension migrate partly into the depressed cross-section 225.

The apparatus 200 may be manufactured on a substrate 227. The substrate 227 may include side walls 228-1 and 228-2, extending along plane 230 and a base 232 extending along plane 234. The substrate 227 may form a channel 229 within which droplets may travel from the droplet generator 209 to the droplet counter 215. A cover 231 may extend along plane 234 to enclose the channel 229. The depressed cross-section 225 may be comprised of a portion of the substrate 227 that has been removed. Although FIGS. 2B and 2C illustrate the depressed cross-section 225 as being rectangular or square shaped, examples are not limited to such geometric shapes.

The trench 206 including the depressed cross-section 225 may permit droplets with a surface tension below the threshold surface tension to migrate to a particular sorting lane among the plurality of sorting lanes, and to travel a length of the apparatus to the droplet counter. For instance, referring to FIG. 2B, a droplet with an interfacial tension between the inside of the droplet and the channel 229 below a threshold, minimizes the droplet area and prevents the droplet from extending into the depressed cross-section 225. When traveling past the trench 206, the droplet is not sorted or directed by the trench 206. In contrast, referring to FIG. 2C, a droplet with an interfacial tension between the inside of the droplet and the channel 229 at or above a threshold, allows the droplet to bulge into the depressed cross-section 225 of the trench 206. When traveling past the trench 206, the droplet moves into or bulges into the depressed cross-section 225 of the trench 206, as illustrated in FIG. 2C. Accordingly, the surface tension-based sorter 213 may include a trench 206, which may include a depressed cross-section in which droplets with a surface tension below a threshold surface tension migrate partly into the depressed cross-section, such that droplets may be sorted by surface-tension.

Figure 2D:
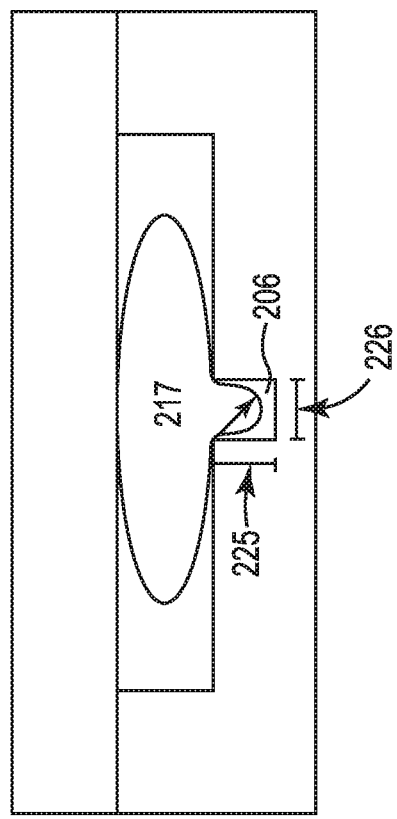
Figure 2E:
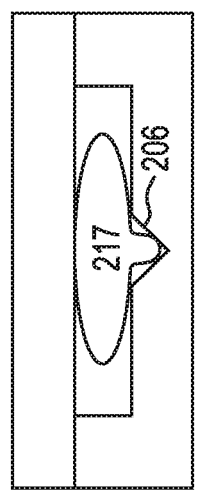
Figure 2F:
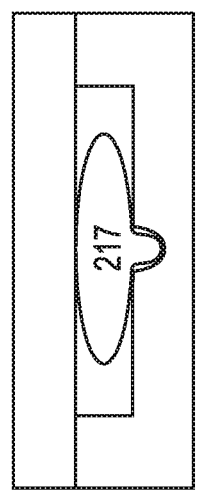
Figure 5A:
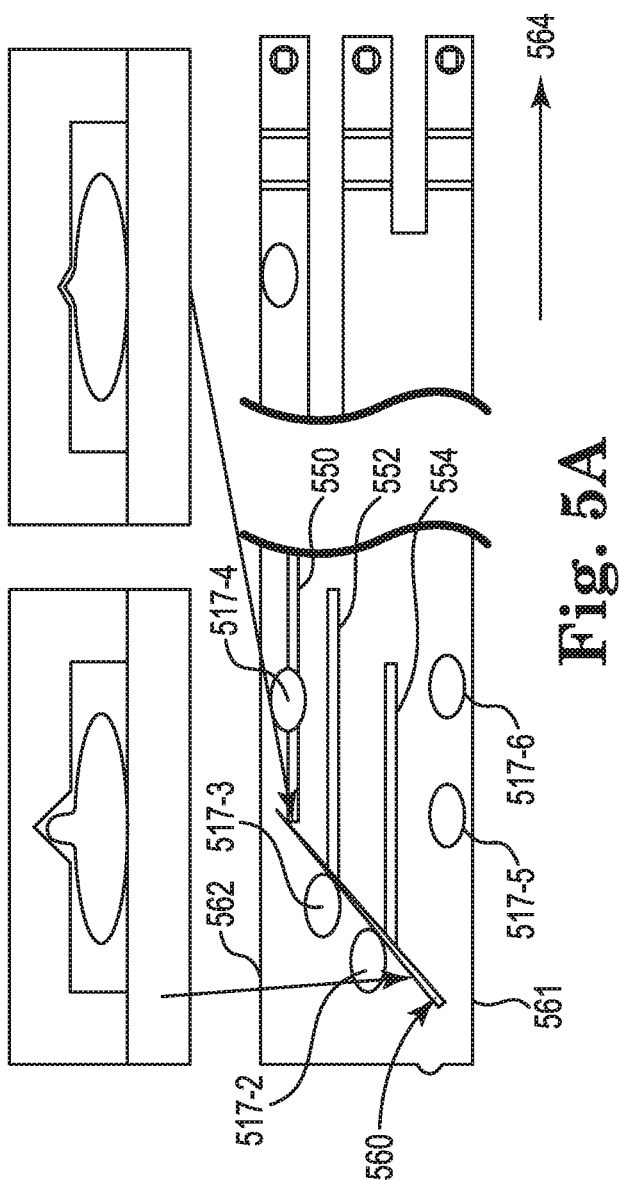
FIGS. 5A and 5B further illustrate example apparatuses for sorting a droplet including a biologic sample, consistent with the present disclosure.
Figure 5B:
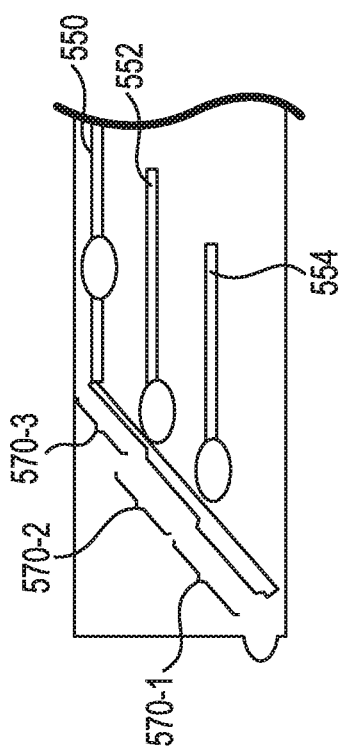

FIGS. 2D, 2E, and 2F further illustrate example cross-sections of surface tension-based sorter 213, along plane 202, consistent with the present disclosure. Each of FIGS. 2D, 2E and 2F illustrate an example manner in which droplets may be sorted by the surface tension-based sorter 213. Particularly, FIG. 2D illustrates the relationship between surface tension of the droplet 217 and the size of the depressed cross-section of trench 206. For instance, as illustrated in FIG. 2D, the depth of the depressed cross-section 225, as well as the width 226 of the trench 206 define the surface tension cut-off for which the droplet either follows the trench 206 or does not. In such a manner, the depth and/or shape of the depressed cross-section may be varied to increase or decrease the likelihood that droplets will follow the trench 206 or not. For instance, as illustrated in FIG. 2E, the trench 206 may have a triangular shaped cross section as opposed to a square or rectangular cross section as illustrated in FIG. 2D. As another illustration, the trench 206 may have a rounded cross section, as illustrated in FIG. 2F. As illustrated in FIGS. 5A, 5B, and elsewhere, the trench 206 may be inverted, relative to the cross-sections illustrated in FIGS. 2A, 2B, 2C, 2D, 2E, and 2F. For instance, the cover 231 may comprise a bottom surface of the surface tension-based sorter, and the substrate 227 including the depressed cross-section may comprise a top surface of the surface tension-based sorter.

Figure 3A:
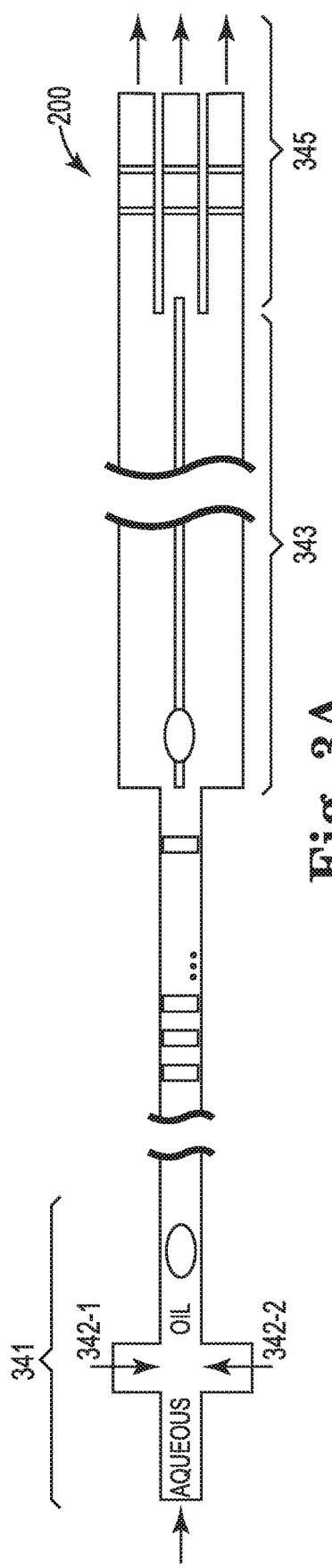
FIGS. 3A, 3B and 3C further illustrate example apparatuses for sorting a droplet including a biologic sample, consistent with the present disclosure.
Figure 3B:
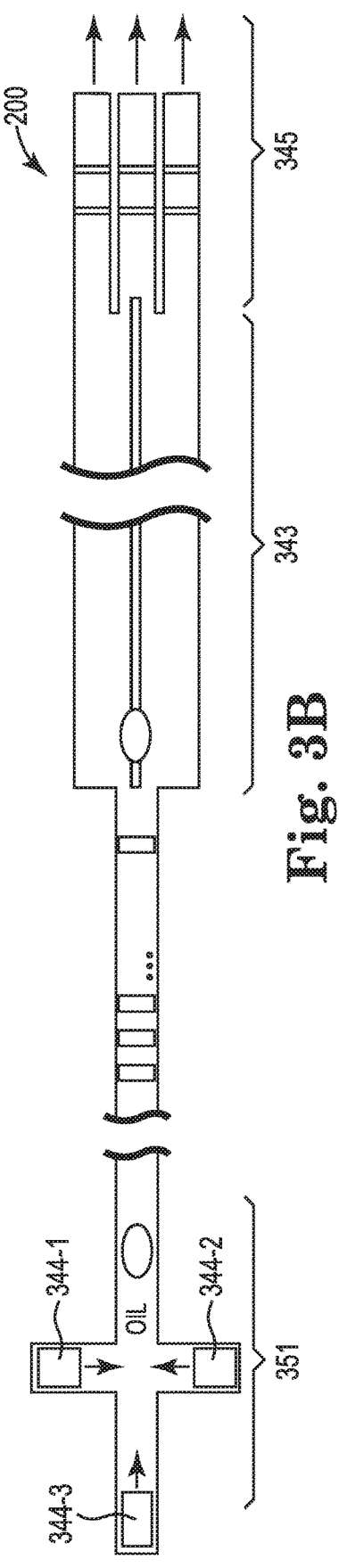
Figure 3C:
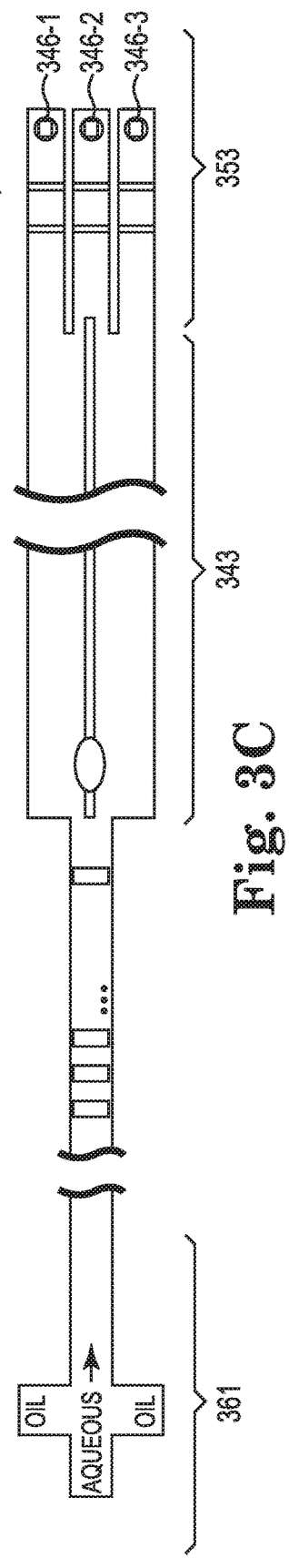

FIGS. 3A, 3B and 3C further illustrate example apparatuses for sorting a droplet including a biologic sample, consistent with the present disclosure. Each of FIGS. 3A, 3B, and 3C illustrate additional and/or alternative constructs for the apparatus. Particularly, each of FIGS. 3A, 3B, and 3C illustrate additional and/or alternative constructs of the apparatus, including use of pumps to generate a flow within the apparatus.

As a particular illustration, FIG. 3A illustrates an apparatus 200 including a droplet generator 341 including external pumps. Although not illustrated in FIG. 3A, a first pump 342-1 and a second pump 342-2 may be disposed on opposing sides of the apparatus. Each of pump 342-1 and pump 342-2 may include an inertial pump, a piezoelectric element, a thermal resistor, or other device to move fluid through the apparatus from the droplet generator 341 to the surface tension-based sorter 343, and the droplet counter 345. Particularly, pumps 342-1 and 342-2 may pump oil through the apparatus 200, such as may be implemented in ddPCR. The droplet generator 341 may form aqueous droplets which float in the oil, within apparatus 200. The pumps illustrated in FIG. 3A are disposed outside of the apparatus. The end of the apparatus opposite of the droplet generator 341 and downflow from the droplet counter 345, may empty into a waste reservoir and/or empty into a reservoir for further analysis.

As another illustration, FIG. 3B illustrates an apparatus 200 including a droplet generator 351 in which pumps may be integrated into part of the droplet generator to generate a fluid flow through the apparatus. Pumps 344-1, 344-2, and 344-3 may be disposed in differing portions of the droplet generator 351. For instance, pump 344-1 and pump 344-2 may be disposed on orthogonal inputs of the droplet generator 351 as illustrated, whereas pump 344-3 may be disposed on a parallel input of the droplet generator 351 as illustrated. The parallel input in which pump 344-3 is disposed, may also include an opening for input of the biologic sample. As described with regards to FIG. 3A, each of pump 344-1, pump 344-2, and pump 344-3 may include an inertial pump, a piezoelectric element, a thermal resistor, or other device to move fluid through the apparatus from the droplet generator 351 to the surface tension-based sorter 343, and the droplet counter 345. The pumps 344-1, 344-2, and 344-3 pump oil through the apparatus 200, as discussed with regards to FIG. 3A.

Yet further, FIG. 3C illustrates an apparatus 200 including a droplet generator 361, a surface tension-based sorter 343, and a droplet counter 353. As discussed with regards to FIGS. 3A and 3B, the droplet generator 361 may generate aqueous droplets suspended in an oil. As opposed to the examples illustrated in FIGS. 3A and 3B, FIG. 3C illustrates an apparatus in which pumps 346-1, 346-2, and 346-3 are disposed at an end of the droplet counter 353 to eject fluid from the apparatus for waste collection and/or for further analysis.

FIGS. 4A, 4B, 4C, 4D, 4E, and 4F further illustrate example apparatuses for sorting a droplet including a biologic sample, consistent with the present disclosure. Each of FIGS. 4A, 4B, 4C, 4D, 4E, and 4F illustrate additional and/or alternative constructs for the apparatus. Particularly, each of 4A, 4B, 4C, 4D, 4E, and 4F illustrate additional and/or alternative constructs of the surface tension-based sorter, consistent with the present disclosure.

Figure 4A:
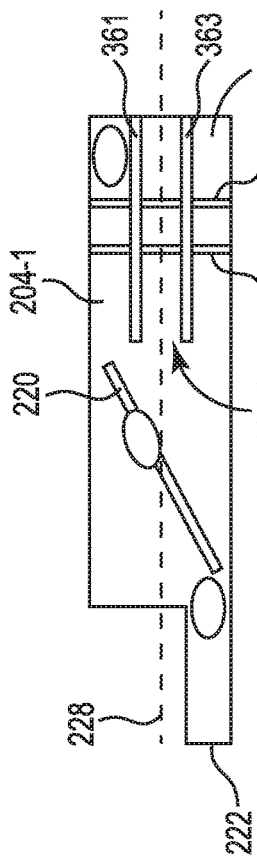
FIGS. 4A, 4B, 4C, 4D, 4E, and 4F further illustrate example apparatuses for sorting a droplet including a biologic sample, consistent with the present disclosure.

As a particular example, FIG. 4A illustrates a construct of the surface tension-based sorter in which the trench (e.g., trench 206 illustrated in FIG. 2A) directs the droplet (e.g., droplet 217 illustrated in FIG. 2A) into a particular sorting lane with counting electrodes. For instance, sorting lanes 204-1, 204-2, and 204-3 may be separated by channels 361 and 363. Trench 206 may extend into sorting lane 204-1 and past a start of channel 361 to ensure that droplet 217 continues in sorting lane 204-1 over counting electrodes 208-1 and 208-2.

Figure 4B:
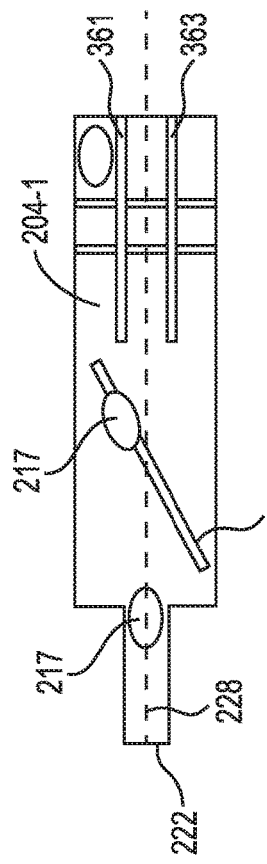
Figure 4C:
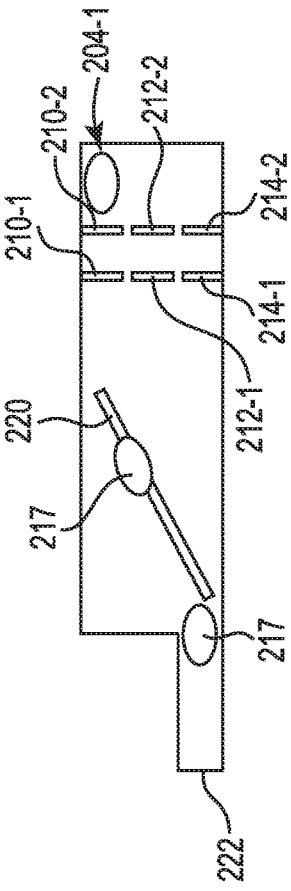

As another illustration, FIG. 4B illustrates a construct of the surface tension-based sorter in which the channels are removed. Rather, the sorting lanes may be delineated by discrete pairs of counting electrodes. For instance, a first sorting lane may be delineated by counting electrodes 210-1 and 210-2, which are separated from counting electrodes 212-1 and 212-2 associated with a second sorting lane and 214-1 and 214-2 associated with a third sorting lane. The trench 206 may extend over counting electrodes 210-1 and 210-2, such that the droplet 217 is conveyed directly over the counting electrodes 210-1 and 210-2 without the use of channels.

In related examples, the trench 206 may extend over the counting electrodes and sorting lanes may be separated by channels. For instance, referring to FIG. 4C, trench 206 may extend over counting electrodes 208-1 and 208-2, and channels 361 and 363 may further separate respective sorting lanes.

Figure 4D:
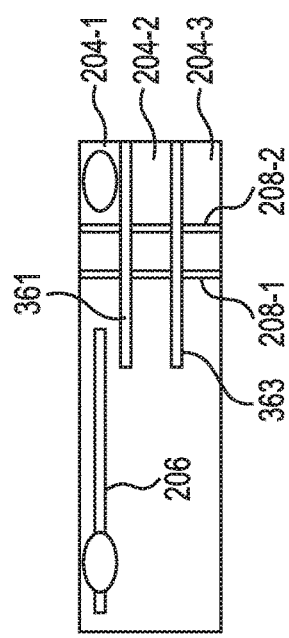
Figure 4E:
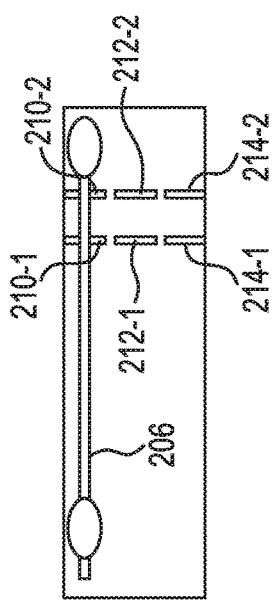

In some examples, the trench may increase likelihood of sorting droplets by surface tension. In such examples, the trench extends tangentially from a median plane of the apparatus. FIG. 4D illustrates an example apparatus including a tangential trench. As illustrated in FIG. 4D, the trench 220 extends at an angle relative to midline 228 of the apparatus, such that droplet 217 travels a length of the trench 220, from input 222 to sorting lane 204-1. In this manner, the trench 220 traverses the apparatus from input 222 to an opposing edge of the apparatus. Droplets with a higher surface tension will not travel along trench 220 and will therefore pass over it and travel to either sorting lane 204-2 or sorting lane 204-3.

Figure 4F:
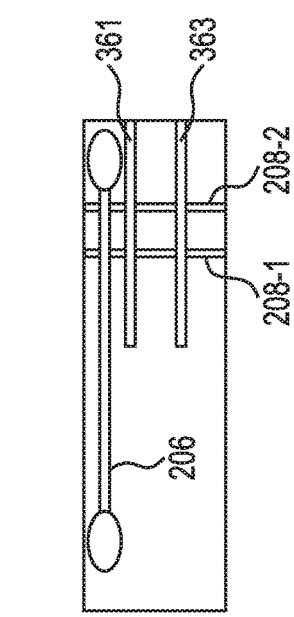

In some examples, the input may be disposed along the median plane of the apparatus. For instance, referring to FIG. 4E, the droplet 217 may travel from input 222, disposed along median 228, to sorting lane 204-1. Moreover, like the example illustrated in FIG. 4B, the sorting lanes may be configured with or without channels between them. As illustrated in FIG. 4F, the droplet 217 may travel from input 222, along the trench 220, and to sorting lane 204-1 without the use of channels. In such examples, each sorting lane may be delineated by separate and discrete counting electrodes. For instance, electrodes 210-1 and 210-2 may be associated with a first sorting lane (204-1), separated from counting electrodes 212-1 and 212-2 associated with a second sorting lane, and separated from counting electrodes 214-1 and 214-2 associated with a third sorting lane.

FIGS. 5A and 5B further illustrate example apparatuses for sorting a droplet including a biologic sample, consistent with the present disclosure. Particularly, FIGS. 5A and 5B illustrate a portion of the apparatus 200, including both a tangential trench and longitudinal trenches. In some examples, the surface tension-based sorter includes a plurality of longitudinal trenches, each longitudinal trench associated with a different respective sorting lane of the plurality of sorting lanes, the surface tension-based sorter further including: a tangential trench extending from the reaction zone to the plurality of longitudinal trenches, wherein each longitudinal trench has a depressed cross-section of uniform width for a length of the trench, and wherein the tangential trench includes a depressed cross-section of decreasing width for a length of the trench. Because the surface tension of the droplets may be directly correlated with the pH of the droplet, droplets with a higher surface tension may attach to a wider and/or deeper trench as opposed to low surface tension droplets.

Referring to FIG. 5A, each of longitudinal trenches 550, 552, and 554 may extend along a length of the apparatus from the reaction zone to the droplet counter. Each of the longitudinal trenches 550, 552, and 554 may be associated with a different respective pH. For instance, longitudinal trench 554 may be associated with a first pH and longitudinal trench 552 may be associated with a second pH, where the second pH is higher than the first pH. Additionally, longitudinal trench 550 may be associated with a third pH that is higher than both the first pH and the second pH. To aid with the sorting of droplets among longitudinal trenches 550, 552, and 554, tangential trench 560 may traverse the apparatus 200. As the tangential trench 560 traverses from a first edge 561 of apparatus 200, to a second edge 562 of apparatus 200, the tangential trench 560 may reduce in width and/or depth. Accordingly, as droplets progress along tangential trench 560, each droplet will leave the tangential trench 560 when the width and/or depth of the trench 560 reduces to an extent at which the surface tension of the droplet prevents the droplet from attaching to the tangential trench 560.

As an illustration, droplets 517-2, 517-3, and 517-4 may each attach to trench 560 at edge 561 of apparatus 200. Each droplet will begin to traverse along tangential trench 560 towards edge 562 of apparatus 200. Droplets 517-5 and 517-6, with a surface tension higher than a threshold level and are unable to attach to tangential trench 560. Accordingly, droplets 517-5 and 517-6 continue in direction 564 towards the counting electrodes. Droplet 517-2, with a surface tension greater than droplets 517-3 and 517-4, but less than droplets 517-5 and 517-6, may traverse along tangential trench 560 until longitudinal trench 554. At the juncture between tangential trench 560 and longitudinal trench 554, the width and/or depth of the tangential trench 560 reduces to a point that prohibits droplet 517-2 from remaining attached to tangential trench 560, at which point droplet 517-2 leaves tangential trench 560 and traverses down longitudinal trench 554 in direction 564 toward the counting electrodes.

Similarly, droplet 517-3, with a surface tension greater than droplet 517-4, but less than droplets 517-2, 517-5 and 517-6, may traverse along tangential trench 560 until longitudinal trench 552. At the juncture between tangential trench 560 and longitudinal trench 552, the width and/or depth of the tangential trench 560 reduces to a point that prohibits droplet 517-3 from remaining attached to tangential trench 560, at which point droplet 517-3 leaves tangential trench 560 and traverses down longitudinal trench 552 in direction 564 toward the counting electrodes.

Additionally, droplet 517-4, with a surface tension less than droplets 517-3, 517-2, 517-5 and 517-6, may traverse along tangential trench 560 until longitudinal trench 550. At the juncture between tangential trench 560 and longitudinal trench 550, the width and/or depth of the tangential trench 560 reduces to a point that prohibits droplet 517-4 from remaining attached to tangential trench 560, or to an end of tangential trench 560, at which point droplet 517-4 leaves tangential trench 560 and traverses down longitudinal trench 550 in direction 564 toward the counting electrodes.

While FIG. 5A illustrates tangential trench 560 continuously tapering in width as tangential trench 560 progresses from side 561 to side 562 of apparatus 200, the tangential trench may include a plurality of discrete profile changes. For instance, as illustrated in FIG. 5B, the tangential trench may include a plurality of tangential trenches 570-1, 570-2, and 570-3, arranged by decreasing profiles. Tangential trench 570-1 is illustrated in FIG. 5B as having the greatest width relative to tangential trench 570-2 and tangential trench 570-3. Like the example illustrated in FIG. 5A, each droplet may traverse from tangential trench 570-1, 570-2, and 570-3 until the width and/or depth of the trench is reduced to an extent that the droplet may no longer remain attached, and the droplet traverses along one of longitudinal trench 550, longitudinal trench 552, or longitudinal trench 554.

Figure 6A:
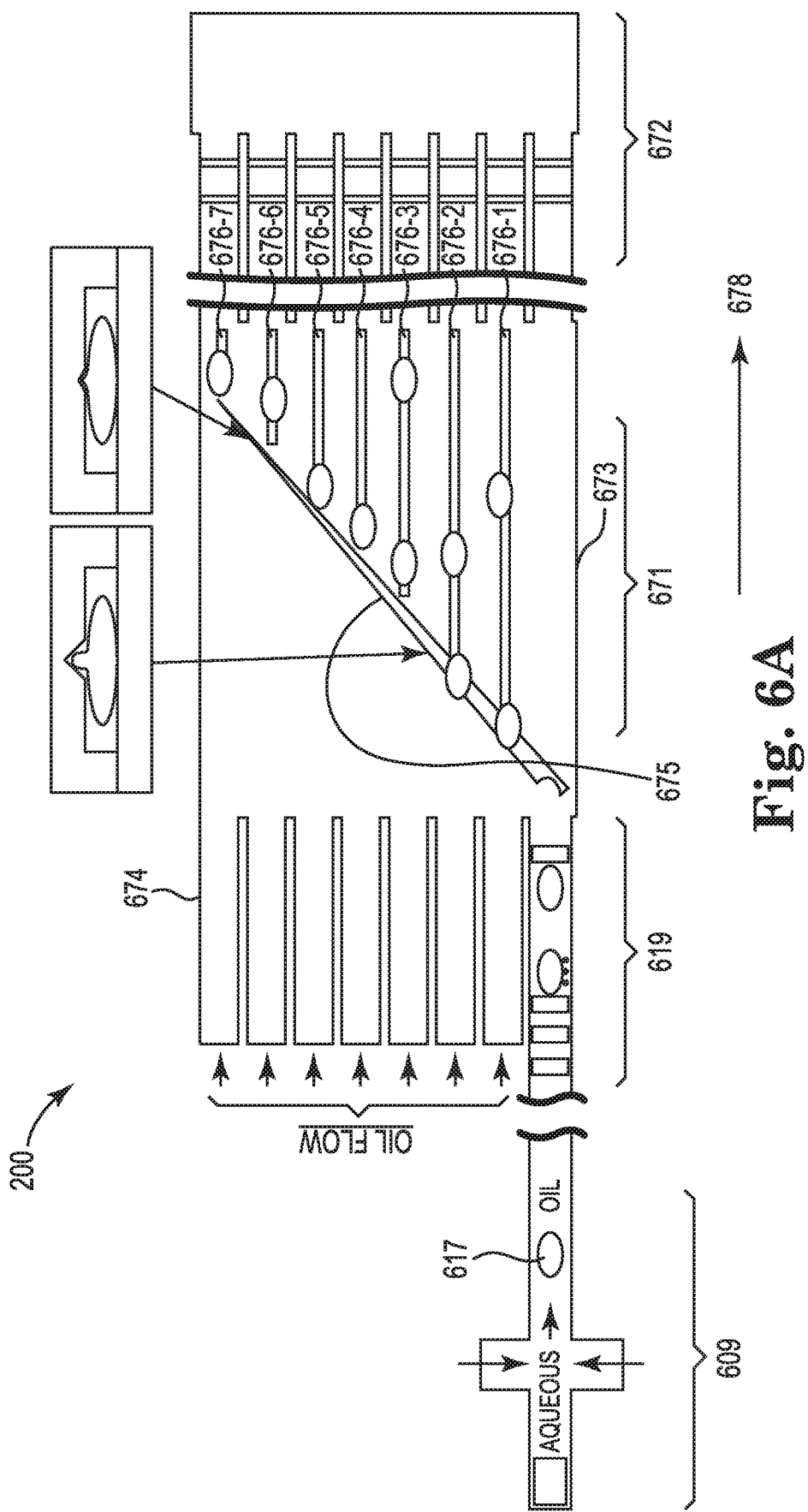
FIGS. 6A and 6B illustrate example apparatuses for sorting a droplet including a biologic sample, consistent with the present disclosure.
Figure 6B:
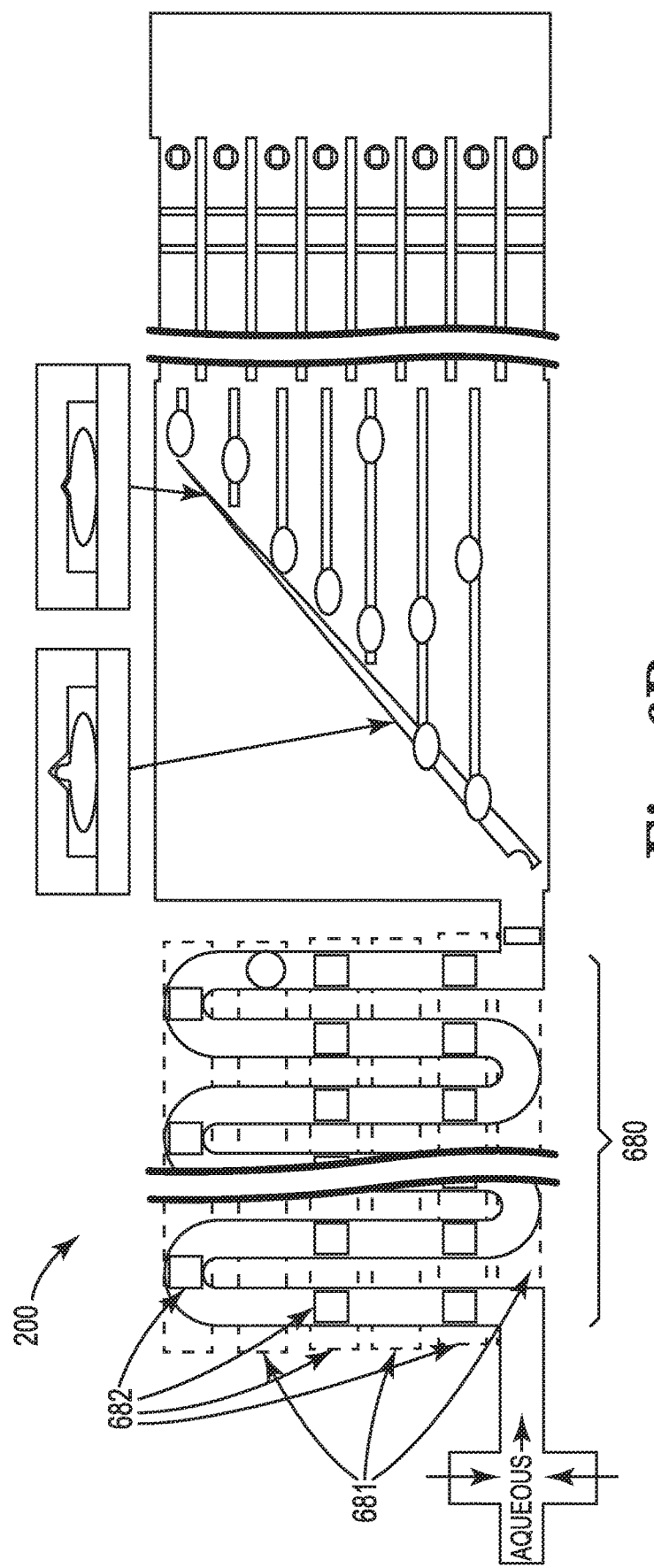

FIGS. 6A and 6B illustrate example apparatuses for sorting a droplet including a biologic sample, consistent with the present disclosure. In the example illustrated in FIG. 6A, a change in the trench profile allows droplets to be sorted based on surface tension and therefore pH. Droplets with a higher amount of nucleic acids will have a higher pH and therefore can be sorted accordingly. The apparatus illustrated in FIG. 6A may enable differentiation of 2-2.5 order of concentration range, which may enable semiquantitative detection of nucleic acid targets. The apparatus 200 may operate at a fixed number of PCR cycles or on a particular amount of amplification time.

For instance, the apparatus 200 may include a droplet generator 609, a reaction zone 619, a surface tension-based sorter 671, and a droplet counter 672. As discussed herein, the droplet generator 609 may generate droplets including a biologic sample and a pH sensitive surfactant, among other components. As illustrated in FIG. 6A, the droplet generator 609 may be disposed along a side edge 673 of apparatus 200. As discussed herein, the droplet generator 609 may form aqueous droplets, which are suspended in oil. As such, oil may be provided to apparatus 200 from an external supply.

Droplets including a biologic sample and a pH sensitive surfactant, among other components may be formed using microwell plates, capillaries, oil emulsion, and arrays of miniaturized chambers with nucleic acid binding surfaces, among others.

As the droplets migrate in direction 678, each respective droplet may undergo a series of heating and cooling cycles to facilitate nucleic acid amplification within reaction zone 619. Once the droplets leave reaction zone 619, a series of trenches sort the droplets by surface tension, and therefore pH.

As an illustration, tangential trench 675 traverses from side 673 of apparatus 200 to side 674 of apparatus 200. As tangential trench 675 traverses the apparatus 200, the depth and/or width of the trench reduces such that droplets with a lower surface tension and therefore a higher pH remain on the trench relative to droplets with a higher surface tension and therefore a lower pH. Accordingly, each of longitudinal trenches 676-1, 676-2, 676-3, 676-4, 676-5, 676-6, and 676-7 may be associated with a different respective pH. As a non-limiting example, longitudinal trench 676-1 may be associated with a pH of 1.0, longitudinal trench 676-2 may be associated with a pH of 2.0, longitudinal trench 676-3 may be associated with a pH of 3.0, longitudinal trench 676-4 may be associated with a pH of 4.0, longitudinal trench 676-5 may be associated with a pH of 5.0, longitudinal trench 676-6 may be associated with a pH of 6.0, and longitudinal trench 676-7 may be associated with a pH of 7.0. Accordingly, droplets with a higher pH and therefore a lower surface tension, will be sorted by longitudinal trenches near edge 674, whereas droplets with a lower pH and therefore a higher surface tension, will be sorted by longitudinal trenches near edge 673. Each longitudinal trench may be associated with a different respective sorting lane in the droplet counter 672, such that the number of droplets in each respective lane may be counted.

Similarly, FIG. 6B illustrates an example for sorting droplets based on surface tension and therefore pH. In contrast to the example illustrated in FIG. 6A, FIG. 6B illustrates an apparatus 200 with an elongated path in the reaction zone 680. In various examples, the reaction zone 680 includes a plurality of hot zones 682 and a plurality of cold zones 681 arranged to heat and cool the biologic sample according to a nucleic acid amplification protocol. In other words, the reaction zone includes a plurality of hot zones and a plurality of cold zones that allow the apparatus 200 to operate at a defined number of heating and cooling cycles for PCR, or for a set amount of amplification time. To enable the specified number of cycles or continuous exposure to elevated temperatures, the elongated path and periodic heat and cold zones can be used. This approach may be beneficial for isothermal amplification processes, because exposure time may be adjusted by the microfluidic path (e.g., by increasing or decreasing the number of hot and cold zones utilized) or by increasing or decreasing the flow rate in apparatus 200.

Figure 7A:
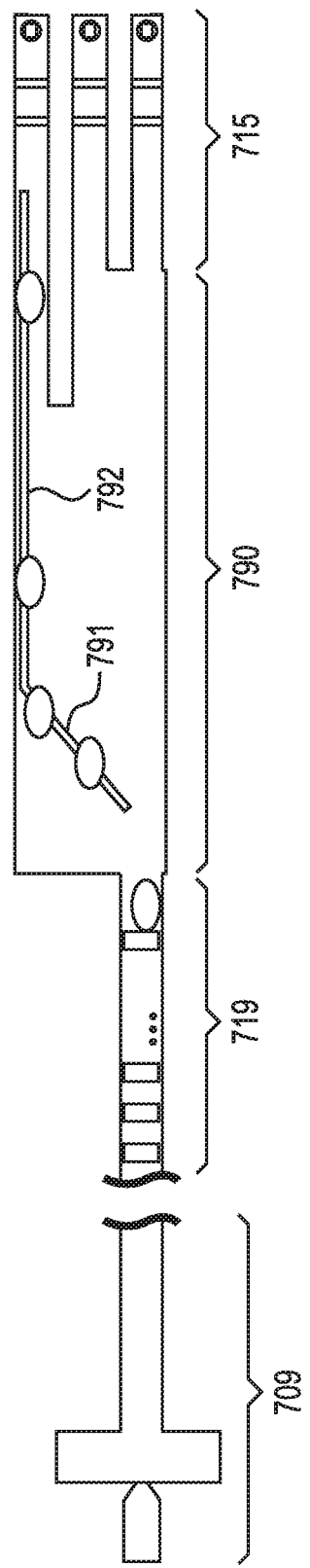

FIGS. 7A, 7B, and 7C illustrate example apparatuses for sorting a droplet including a biologic sample, consistent with the present disclosure. Particularly, FIGS. 7A, 7B, and 7C illustrate various arrangements for the surface tension-based sorter described herein. For instance, FIG. 7A illustrates a droplet generator 709, a reaction zone 719, a surface tension-based sorter 790, and a droplet counter 715. The surface tension-based sorter 790 is illustrated as including a single tangential trench 791 to capture droplets with a surface tension at or below a threshold surface tension and guide the droplets to a longitudinal trench 792 to the droplet counter 715. Each of FIGS. 7B and 7C illustrate a droplet generator 709, a reaction zone 719, and a droplet counter 715. However, FIG. 7B illustrates a surface tension-based sorter 793 including a plurality of tangential trenches 795 to capture droplets with a surface tension at or below a threshold surface tension, as well as a longitudinal trench 796 to guide the droplets to the droplet counter 715. Similarly, FIG. 7C illustrates a surface tension-based sorter 794, including a single trench arranged in a zig-zag sequence to capture droplets with a surface tension at or below a threshold surface tension and direct the droplets to the droplet counter 715.

Figure 8:
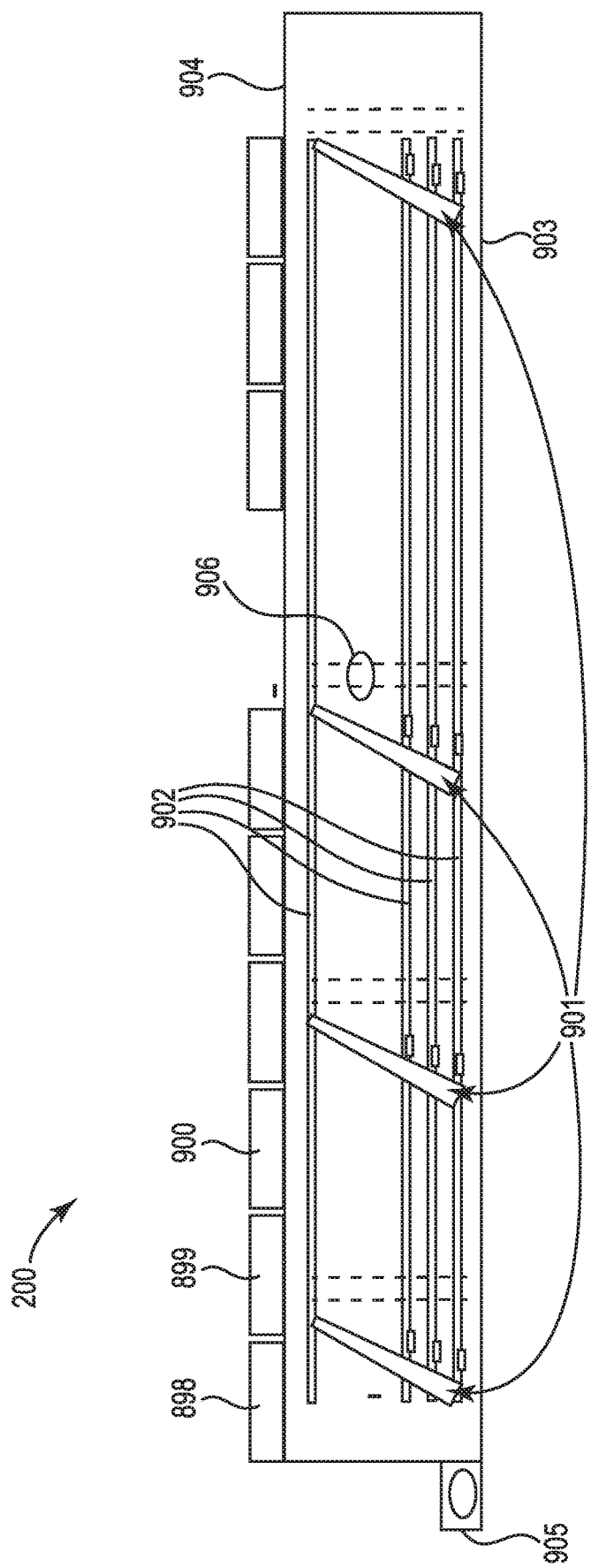
FIG. 8 illustrates an example apparatus for sorting a droplet including a biologic sample, consistent with the present disclosure.

FIG. 8 illustrates an example apparatus for sorting a droplet including a biologic sample, consistent with the present disclosure. In the example illustrated in FIG. 8, droplets enter a zone heated amplification chamber, and are confined to a trench network. As the reaction proceeds and the pH inside the droplet lowers the interfacial tension of the droplet, the droplet accesses higher radii of curvature (e.g., a smaller depth) of trench. The droplet is encouraged to sample high radii of curvature states by a brief increase in radii of curvature (e.g., a decrease in depth) in the longitudinal trenches. The droplet positions are recorded by counting electrodes. The higher the position of the droplet relative to the inlet, the larger the pH change in the droplet and the larger the amount of nucleic acid amplified in the droplet.

For instance, droplets may enter the apparatus at inlet 905, disposed on side 903 of apparatus 200. The apparatus 200 may include a plurality of tangential trenches 901 extending from side 903 to side 904 of apparatus 200. Additionally, apparatus 200 may include a plurality of longitudinal trenches 902 extending a length of apparatus 200. Three distinct temperature zones, zone 898, 899, and 900 may be arranged in a repeating pattern, such that samples are warmed to a first temperature in zone 898, a second temperature at 899, and a third temperature at 900. As the temperature changes, consistent with a nucleic acid amplification protocol, the pH of the droplet will change as the amount of nucleic acid in the droplet increases. Accordingly, the droplet will traverse along one of the tangential trenches 901 to a longitudinal trench 902 based on surface tension (and therefore pH), as described herein. Once a heating cycle is completed, such that a droplet has progressed through zone 898, zone 899, and zone 900, counting electrodes 906 will count the number of droplets in each corresponding sorting lane. As illustrated in FIG. 9, the pattern of heating, sorting, and counting is repeated such that thermal cycling can be repeated, and quantitative measurement of nucleic acids in each droplet may be measured in real-time or near real time.

The term "sample," as used herein, generally refers to any biological material, either naturally occurring or scientifically engineered, which contains at least one nucleic acid which may also include other non-nucleic acid material, such as biomolecules (e.g., proteins, polysaccharides, lipids, low molecular weight enzyme inhibitors, oligonucleotides, primers, templates), polyacrylamide, trace metals, organic solvents, etc. Examples of naturally-occurring samples or mixtures include, but are not limited to, whole blood, blood plasma, and other body fluids, as well as tissue cell cultures obtained from humans, plants, or animals. Examples of scientifically-engineered samples or mixtures include, but are not limited to, lysates, nucleic acid samples eluted from agarose and/or polyacrylamide gels, solutions containing multiple species of nucleic acid molecules resulting either from nucleic acid amplification methods, such as PCR amplification or reverse transcription polymerase chain reaction (RT-PCR) amplification, or from RNA or DNA size selection procedures, and solutions resulting from post-sequencing reactions. However, the sample will generally be a biological sample, which may contain any viral or cellular material, including all prokaryotic or eukaryotic cells, viruses, bacteriophages, mycoplasmas, protoplasts, and organelles. Such biological material may thus comprise all types of mammalian and non-mammalian animal cells, plant cells, algae including blue-green algae, fungi, bacteria, protozoa, etc. Representative samples thus include whole blood and blood-derived products such as plasma, serum and buffy coat, urine, feces, cerebrospinal fluid or any other body fluids, tissues, cell cultures, cell suspensions, etc. The sample may comprise a lysate. The sample may also include relatively pure starting material such as a PCR product, or semi-pure preparations obtained by other nucleic acid recovery processes.

Although specific examples have been illustrated and described herein, a variety of alternate and/or equivalent implementations may be substituted for the specific examples shown and described without departing from the scope of the present disclosure. This application is intended to cover any adaptations or variations of the specific examples discussed herein. Therefore, it is intended that this disclosure be limited only by the claims and the equivalents thereof.

The invention claimed is:

1. An apparatus, comprising:
   a droplet generator to generate a droplet including a biologic sample and a pH sensitive surfactant;
   a reaction zone including a heating array for thermal amplification of a nucleic acid molecule in the biologic sample, the pH sensitive surfactant to change surface tension of the droplet responsive to amplification of the nucleic acid molecule;
   a surface tension-based sorter to sort the droplet into one of a plurality of sorting lanes based on the surface tension of the droplet, wherein a sorting lane among the plurality of sorting lanes is associated with droplets including the amplified nucleic acid molecule; and
   a droplet counter including circuitry to identify whether the droplet includes the amplified nucleic acid molecule by detecting passage of the droplet in one of the plurality of sorting lanes.

2. The apparatus of claim 1, wherein the surface tension-based sorter includes a trench extending from the reaction zone to the droplet counter, the trench including a depressed cross-section in which droplets with a surface tension below a threshold surface tension migrate partly into the depressed cross-section.

3. The apparatus of claim 2, wherein the trench extends to a particular sorting lane among the plurality of sorting lanes, the particular sorting lane assigned to droplets including the amplified nucleic acid molecule, and wherein a remainder of the sorting lanes among the plurality of sorting lanes are assigned to droplets that do not include the amplified nucleic acid molecule.

4. The apparatus of claim 2, wherein the trench including the depressed cross-section is to permit droplets with a surface tension below the threshold surface tension to migrate to a particular sorting lane among the plurality of sorting lanes, and to travel a length of the apparatus to the droplet counter.

5. The apparatus of claim 2, wherein the depressed cross-section of the trench permits droplets with a surface tension at or above the threshold surface tension to travel past the trench, and to travel a length of the apparatus to the droplet counter.

6. An apparatus, comprising:
   a droplet generator to generate a droplet including a biologic sample and a pH sensitive surfactant;
   a reaction zone including a heating array for thermal amplification of a nucleic acid molecule in the biologic sample, the pH sensitive surfactant to change surface tension of the droplet responsive to amplification of the nucleic acid molecule;
   a surface tension-based sorter to sort the droplet into one of a plurality of sorting lanes based on the surface tension of the droplet; and
   a droplet counter including circuitry to detect passage of the droplet in one of the plurality of sorting lanes and count a number of droplets in each of the plurality of sorting lanes.

7. The apparatus of claim 6, wherein the surface tension-based sorter includes a trench extending from the reaction zone to the droplet counter, the trench including a depressed cross-section in which droplets with a surface tension below a threshold surface tension migrate partly into the depressed cross-section.

8. The apparatus of claim 7, wherein the trench extends tangentially from a median plane of the apparatus.

9. The apparatus of claim 6, wherein the surface tension-based sorter includes a plurality of longitudinal trenches, each longitudinal trench associated with a different respective sorting lane of the plurality of sorting lanes, the surface tension-based sorter further including:
   a tangential trench extending from the reaction zone to the plurality of longitudinal trenches;
   wherein each longitudinal trench has a depressed cross-section of uniform width for a length of the trench, and wherein the tangential trench includes a depressed cross-section of decreasing width for a length of the trench.

10. The apparatus of claim 6, wherein the reaction zone includes a plurality of hot zones and a plurality of cold zones arranged to heat and cool the biologic sample according to a nucleic acid amplification protocol.

* * * * *